US010604723B2

(12) United States Patent
Eldredge et al.

(10) Patent No.: US 10,604,723 B2
(45) Date of Patent: Mar. 31, 2020

(54) CATIONIC CARBOHYDRATE POLYMERS FOR FABRIC CARE

(71) Applicants: Rohm and Haas Company, Philadelphia, PA (US); Union Carbide Corporation, Seadrift, TX (US)

(72) Inventors: Josephine Eldredge, Norristown, PA (US); John Hayes, Collegeville, PA (US); Emmett M. Partain, III, Bound Brook, NJ (US); Jan E. Shulman, Newtown, PA (US); Jennifer J. Todd, Willow Grove, PA (US)

(73) Assignees: Rohm and Haas Company, Philadelphia, PA (US); Union Carbide Corporation, Seadrift, TX (US)

(*) Notice: Subject to any disclaimer, the term of this patent is extended or adjusted under 35 U.S.C. 154(b) by 71 days.

(21) Appl. No.: 15/523,700

(22) PCT Filed: Nov. 9, 2015

(86) PCT No.: PCT/US2015/059692
§ 371 (c)(1),
(2) Date: May 2, 2017

(87) PCT Pub. No.: WO2016/077207
PCT Pub. Date: May 19, 2016

(65) Prior Publication Data
US 2017/0335242 A1    Nov. 23, 2017

Related U.S. Application Data

(60) Provisional application No. 62/077,966, filed on Nov. 11, 2014.

(51) Int. Cl.
| C11D 1/00 | (2006.01) |
| C11D 3/22 | (2006.01) |
| C11D 3/00 | (2006.01) |
| C07C 211/63 | (2006.01) |
| C08L 1/28 | (2006.01) |

(52) U.S. Cl.
CPC ............ *C11D 3/227* (2013.01); *C07C 211/63* (2013.01); *C08L 1/284* (2013.01); *C11D 3/0021* (2013.01); *C11D 3/0036* (2013.01)

(58) Field of Classification Search
None
See application file for complete search history.

(56) References Cited

U.S. PATENT DOCUMENTS

| 4,773,939 A | 9/1988 | Meffert et al. | |
| 6,833,347 B1 * | 12/2004 | Wang | C11D 3/227 510/276 |
| 6,949,498 B2 * | 9/2005 | Murphy | C11D 1/02 510/327 |
| 7,056,879 B2 | 6/2006 | Wang et al. | |
| 2010/0132132 A1 | 6/2010 | Zhang et al. | |
| 2010/0313360 A1 * | 12/2010 | Menting | C11D 1/83 8/137 |
| 2011/0319310 A1 * | 12/2011 | Labeque | C11D 3/227 510/296 |
| 2011/0319314 A1 * | 12/2011 | Labeque | C11D 3/3773 510/527 |
| 2015/0299619 A1 | 10/2015 | Partain, III et al. | |

FOREIGN PATENT DOCUMENTS

| EP | 2004785 A1 | 12/2008 |
| EP | 2399978 | * 12/2011 |
| WO | WO2011163371 | * 12/2011 |
| WO | 2014052396 A1 | 4/2014 |
| WO | 2014079621 A1 | 5/2014 |
| WO | WO2015065809 | * 5/2015 |

* cited by examiner

*Primary Examiner* — Necholus Ogden, Jr.
(74) *Attorney, Agent, or Firm* — Kenneth Crimaldi

(57) ABSTRACT

A fabric care composition comprising a modified carbohydrate polymer having quaternary ammonium groups having at least one $C_8$-$C_{22}$ alkyl or alkenyl group. The modified carbohydrate polymer has a weight-average molecular weight of at least 500,000.

10 Claims, No Drawings

CATIONIC CARBOHYDRATE POLYMERS FOR FABRIC CARE

This invention relates to cationically-modified carbohydrate polymers as fabric care additives.

Use of cationic carbohydrate polymers in laundry detergents is known, as in, e.g., U.S. Pat. No. 6,833,347. However, this reference does not suggest the use of the modified polymers described herein.

The problem solved by this invention is the deposition of soils in fabric care compositions containing cationic compounds, which often resulted in clothes appearing gray or dingy after laundering.

STATEMENT OF INVENTION

The present invention provides a fabric care composition comprising at least one modified carbohydrate polymer having quaternary ammonium groups having at least one $C_8$-$C_{22}$ alkyl or alkenyl group; wherein modified carbohydrate polymers have a weight-average molecular weight of at least 500,000; and wherein at least 20 wt % of quaternary ammonium groups on said at least one modified carbohydrate polymer have at least one $C_8$-$C_{22}$ alkyl or alkenyl group.

DETAILED DESCRIPTION

Percentages are weight percentages (wt %) and temperatures are in ° C., unless specified otherwise. Operations were performed at room temperature (20-25° C.), unless specified otherwise. The detergent may be a powder, tablet, liquid, unit dose or gel. An "alkyl" group is a saturated, substituted or unsubstituted hydrocarbyl group having from one to twenty-two carbon atoms in a linear or branched arrangement. Alkyl groups are unsubstituted unless otherwise specified. An "alkenyl" group is an alkyl group having at least one carbon-carbon double bond, preferably one carbon-carbon double bond. The "modified carbohydrate polymer" is a carbohydrate polymer which has been functionalized with quaternary ammonium groups having at least one $C_8$-$C_{22}$ alkyl or alkenyl group.

At least 20 wt % of quaternary ammonium groups on said at least one modified carbohydrate polymer have at least one $C_8$-$C_{22}$ alkyl or alkenyl group, i.e., at least 20 wt % of all quaternary ammonium groups on all of the modified carbohydrate polymers in the composition have at least one $C_8$-$C_{22}$ alkyl or alkenyl group. Preferably at least 30 wt % of quaternary ammonium groups on said at least one modified carbohydrate polymer have at least one $C_8$-$C_{22}$ alkyl or alkenyl group, preferably at least 40 wt %, preferably at least 50 wt %, preferably at least 60 wt %, preferably at least 70 wt %, preferably at least 80 wt %, preferably at least 90 wt %.

Preferably, the carbohydrate polymer is an alkyl cellulose ether, hydroxyalkyl cellulose ether, guar gum, locust bean gum, xanthan gum, amylose, amylopectin, or dextran. In the alkyl cellulose ethers, preferably the alkyl ether groups are $C_1$-$C_4$ alkyl; preferably $C_1$-$C_3$ alkyl; preferably methyl, ethyl; in hydroxyalkyl cellulose ethers, preferably the hydroxyalkyl groups are 2-hydroxyethyl or 2-hydroxypropyl. More than one type of alkyl or hydroxyalkyl group may be present on a cellulose ether. Especially preferred cellulose ethers include, e.g., methylcellulose (MC), ethylcellulose (EC), ethyl methyl cellulose, hydroxyethyl cellulose (HEC), hydroxypropyl cellulose (HPC), hydroxyethyl methyl cellulose (HEMC), hydroxypropyl methyl cellulose (HPMC), ethyl hydroxyethyl cellulose (EHEC), and carboxymethyl cellulose (CMC). HEC, HPMC, HEMC, and MC are preferred cellulose-based polymers. Specific examples of preferred cellulose based polymers include CELLOSIZE HEC, METHOCEL HPMC, and WALOCEL HEMC polymers commercially available from The Dow Chemical Company. The number of alkyl ether or hydroxyalkyl groups per glucopyranosyl unit is determined by analysis of the polymer. For example, for METHOCEL HPMC polymers the determination of the % methoxyl and % hydroxypropoxyl in hydroxypropyl methylcellulose is carried out according to the United States Pharmacopeia (USP 32). The values obtained are % methoxyl and % hydroxypropoxyl. These are subsequently converted into degree of substitution (DS) for methyl substituents and molar substitution (MS) for hydroxypropyl substituents. Residual amounts of salt and moisture have been taken into account in the conversion. The preferred % methoxyl varies between 10% and 35%, and the preferred % hydroxypropoxyl varies between 0 and 40%. For CELLOSIZE HEC polymers, the determination of the ethylene oxide molar substitution (EO MS) can be conducted using the Zeisel method as described in ASTM D-4794. The preferred EO MS varies between 0.5 and 5.0, preferably 1.5 to 3.5.

Preferably, an alkyl cellulose ether or a hydroxyalkyl cellulose ether has an average degree of substitution of 1.0 to 2.5 $C_1$-$C_6$ alkyl ether groups per glucopyranosyl unit; preferably it has a viscosity, measured from a 1 wt % solution in water at 20° C., of 10 to 100,000 mPa·s, preferably 50 to 7,000, preferably 100 to 6,000. Aqueous solution viscosities were measured for these cellulose ethers using either a Brookfield LVT viscometer at 25° C. and 30 rpm or according to United States Pharmacopeia (USP 35, "Hypromellose", pages 3467-3469) followed by an Ubbelohde viscosity measurement according to DIN 51562-1: 1999-01 (January 1999). Viscosities of cellulose ethers have been correlated with molecular weights, and accordingly, one skilled in the art would understand the meaning of either measurement. See C. M. Keary, *Carbohydrate Polymers*, vol. 45 (2001), pages 293-303. Cellulose polymers contain repeat units having a 1,4'-β-glucopyranosyl structure, also known as anhydroglucose.

Preferably, the alkyl or hydroxyalkyl cellulose ether is of formula (I)

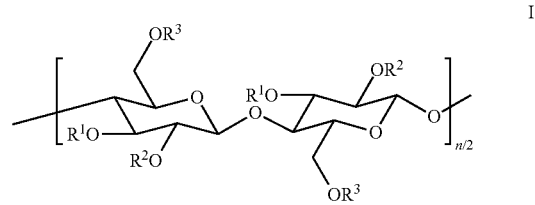

wherein $R^1$, $R^2$ and $R^3$ are independently selected from: hydrogen, alkyl or hydroxyalkyl; wherein alkyl groups may comprise from one to six carbon atoms which may be unsubstituted or substituted with carboxylic acid or salts thereof (attached to alkyl via carbon, e.g., carboxymethyl cellulose), halo or $C_1$-$C_4$ alkoxy; and n (also known as the "degree of polymerization") is from 25 to 7,500. Preferably, alkyl groups are unsubstituted. Preferably, n is from 2000 to 7,000, preferably 3,000 to 6,500. Preferably, alkyl groups have from one to four carbon atoms, preferably from one to three. Preferably, the modified carbohydrate polymer has a weight-average molecular weight of at least 700,000, preferably at least 800,000, preferably no greater than 2,500,000, preferably no greater than 2,000,000.

The modified carbohydrate polymer has quaternary ammonium substituents attached to carbohydrate hydroxyl groups via a linker. Preferably, the linker is a $C_2$-$C_{12}$ aliphatic group, a 2-hydroxypropyl group [—$CH_2$—CHOH—$CH_2$—], a polyethylene glycol group [(—$CH_2$—$CH_2$—O—)$_x$] where x is 1 to 10 (preferably 1 to 6). Preferably, the modified carbohydrate polymer is of formula (I) above, wherein a quaternary ammonium substituent attached to a linker is one of the choices for $R^1$, $R^2$ or $R^3$; preferably $R^3$. Preferably, the degree of substitution of the quaternary ammonium substituent is from 0.01 to 1; preferably at least 0.02, preferably at least 0.03, preferably at least 0.04, preferably at least 0.05; preferably no greater than 0.5, preferably no greater than 0.3, preferably no greater than 0.25.

Carbohydrate polymer having quaternary ammonium groups may be prepared by applying alkylation methods known in the art, e.g., alkylation of a carbohydrate hydroxyl group with either an epoxy-functionalized quaternary ammonium salt or a chlorohydrin-functionalized quaternary ammonium salt in the presence of a suitable base. Examples of chlorohydrin-functionalized quaternary ammonium salts useful in the present invention include the QUAB 342, 360 and 426 compounds available from SKW Chemicals Inc. Epoxy-functional quaternary ammonium salt comprise a quaternary ammonium salt and a substituent which includes an epoxide ring; they include, e.g., a quaternary ammonium salt having an epoxyalkyl group chemically bound as one of the quaternary substituents. Similarly, a chlorohydrin-functionalized quaternary ammonium salt has a vicinal halohydroxy group chemically bound as a quaternary substituent. For example, a quaternary ammonium substituted hydroxyethyl cellulose ether may be prepared according to the following example reaction scheme where $R^1$ and $R^2$ are hydrogen and $R^3$ is —$CH_2$—$CH_2$—OH, and the HEC polymer is alkylated with 3-chloro-2-hydroxypropyl alkyldimethylammonium chloride,

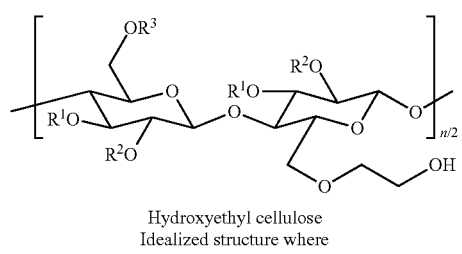

Hydroxyethyl cellulose
Idealized structure where $R^3 =$ —$CH_2$—$CH_2$—OH

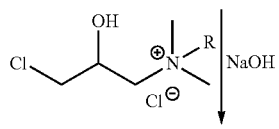

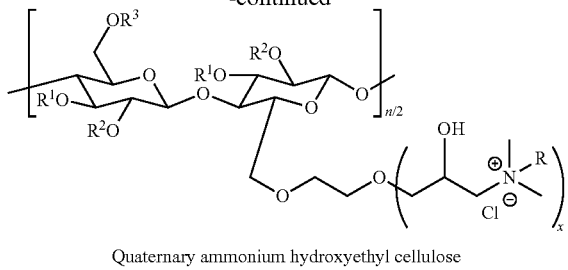

Quaternary ammonium hydroxyethyl cellulose wherein $R^1$ and $R^2$ are hydrogen and $R^3$ is a hydroxyethyl group (—$CH_2$—$CH_2$—OH) as defined previously, and R is a $C_8$-$C_{22}$ alkyl group with x being the degree of substitution for the quaternary ammonium group. The brackets around the two glucopyranosyl units indicate that these are the repeat units of a polysaccharide polymer with a degree of polymerization (DP) with a value of n. Chemical reactions of polysaccharides are usually conducted heterogeneously in which the polymer is suspended in an aqueous organic diluent. Diluents which may be useful in the synthesis of these modified polysaccharides include water-soluble polar organic solvents such as methanol, ethanol, 1-propanol, 2-methyl-2-propanol, 2-butanone and tetrahydrofuran; preferably acetone or 2-propanol. To effect sufficient swelling of the polysaccharide, some amount of water in the diluent is desirable. Suitable bases include, e.g., metal (especially alkali metal) hydroxides, preferably sodium hydroxide. Preferably, the reaction is carried out at a temperature from 10° C. to 100° C., preferably from 15° C. to 70° C. To some degree all the hydroxyl groups in the cellulose ether polymer are susceptible to alkylation by an ammonium salt-containing alkylating agent. Therefore, multiple alkylations at different positions around a given glucopyranosyl unit are possible, and some of the glucopyranosyl units would be unreactive to alkylation and thus contain no quaternary ammonium substituents. The same approach as in the example shown here is possible with many polysaccharides including starch, guar gum (II), locust bean gum, and xanthan gum.

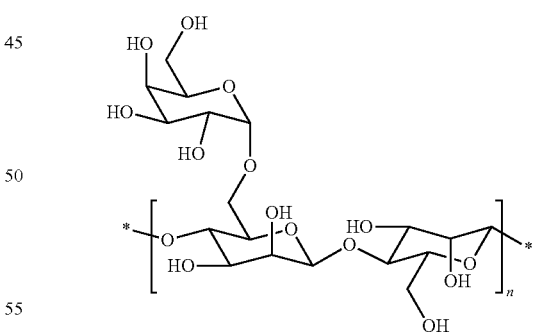

Quaternary ammonium substituents on the carbohydrate polymer have at least one $C_8$-$C_{22}$ alkyl or alkenyl group, preferably one $C_{10}$-$C_{20}$ alkyl or alkenyl group (i.e., each quaternary ammonium substituent has one $C_{10}$-$C_{20}$ alkyl or alkenyl group, although there may be some quaternary substituents that do not have this group), preferably one $C_8$-$C_{22}$ alkyl group, preferably one $C_{10}$-$C_{22}$ alkyl group, preferably one $C_{12}$-$C_{18}$ alkyl group. Preferably, the other substituents on a quaternary ammonium group are methyl groups.

Preferably, the fabric care composition comprises at least 0.1 wt % of the functionalized carbohydrate polymer, preferably at least 0.2 wt %, preferably at least 0.3 wt %, preferably at least 0.4 wt %, preferably at least 0.5 wt %, preferably at least 0.6 wt %, preferably at least 0.7 wt %; preferably no more than 3 wt %, preferably no more than 2.5 wt %, preferably no more than 2 wt %, preferably no more than 1.5 wt %.

Preferably, the fabric care composition is a laundry detergent, a 2-in-1 detergent with added fabric softening agent, or a rinse added fabric softener; preferably a laundry detergent. Preferably, the detergent comprises at least 8 wt % surfactants, preferably at least 10 wt %, preferably at least 12 wt %, preferably at least 15 wt %, preferably at least 20 wt %, preferably at least 30 wt %, preferably at least 40 wt %, preferably at least 50 wt %, preferably at least 60 wt %, preferably at least 70 wt %, preferably at least 75 wt %, preferably at least 80 wt %. Preferably, the detergent comprises no more than 90 wt % surfactants, preferably no more than 85 wt %, preferably no more than 80 wt %, preferably no more than 70 wt %, preferably no more than 60 wt %, preferably no more than 50 wt %, preferably no more than 40 wt %, preferably no more than 30 wt %, preferably no more than 25 wt %, preferably no more than 20 wt %, preferably no more than 17 wt %. In a preferred embodiment of the invention, the detergent comprises from 10 to 30 wt % surfactants, preferably from 12 to 25 wt %. In another preferred embodiment, the detergent comprises from 75 to 90 wt % surfactants, preferably from 80 to 85 wt %.

Preferably, the detergent comprises at least 40 wt % water, preferably at least 45 wt %, preferably at least 50 wt %, preferably at least 55 wt %, preferably at least 60 wt %, preferably at least 65 wt %, preferably at least 70 wt %; preferably no more than 86 wt %, preferably no more than 83 wt %, preferably no more than 79 wt %, preferably no more than 76 wt %, preferably no more than 73 wt %, preferably no more than 70 wt %. In a preferred embodiment of the invention, the detergent comprises from 55 to 86 wt % water, preferably from 60 to 83 wt %. In another preferred embodiment, the detergent comprises no more than 10 wt % water, preferably no more than 6 wt %, preferably no more than 4 wt %.

The detergent may also comprise hydrotropes (e.g., ethanol, propylene glycol), enzymes (e.g., protease, lipase, amylase), preservatives, perfumes, fluorescent whitening agents, dyes and additive polymers (e.g., anti-redeposition polymers, anti-graying polymers). In one preferred embodiment of the invention, the detergent composition comprises from 5 to 20 wt % propylene glycol; preferably at least 7 wt %, preferably at least 9 wt %; preferably no more than 18 wt %, preferably no more than 16 wt %. In another preferred embodiment of the invention, the detergent composition comprises from 1 to 10 wt % propylene glycol; preferably at least 2 wt %, preferably at least 3 wt %; preferably no more than 8 wt %, preferably no more than 6 wt %. In addition, the composition may contain other co-solvents (e.g., ethanol), amines (e.g., monoethanolamine, triethanolamine, MiPA, DiPA, TiPA, AMP-95) and organic sulfonates (sodium toluene, cumene and xylene). Preferably, the detergent composition comprises from 0.5 to 8 wt % of these other co-solvents; preferably at least 1 wt %, preferably at least 2 wt %; preferably no more than 6 wt %, preferably no more than 4 wt %.

The surfactant(s) may be cationic, anionic, nonionic, fatty acid metal salt, zwitterionic or betaine surfactants. Preferably, the surfactant comprises at least one surfactant selected from anionic and nonionic surfactants, preferably at least two. Preferably, nonionic surfactants have an alkyl group having at least eight carbon atoms and at least five polymerized ethylene oxide or propylene oxide residues. Preferably, nonionic surfactants have at least five polymerized ethylene oxide residues, preferably at least six, preferably at least seven, preferably at least eight; preferably no more than twelve, preferably no more than eleven, preferably no more than ten. In a preferred embodiment of the invention, the detergent composition comprises at least 48 wt % alcohol ethoxylates, preferably at least 51 wt %, preferably at least 54 wt %; preferably no more than 67 wt %, preferably no more than 65 wt %. In another preferred embodiment of the invention, the detergent comprises from 1 to 7 wt %, preferably from 1.5 to 5.5 wt %. Preferably, an alcohol ethoxylate has a $C_8$-$C_{18}$ alkyl group, preferably $C_{10}$-$C_{16}$, preferably $C_{12}$-$C_{15}$. Preferably the alkyl groups are linear. Preferably, a linear alcohol ethoxylate contains from five to nine polymerized units of ethylene oxide, preferably seven. Preferably, anionic surfactants have an alkyl group having at least ten carbon atoms and an anionic group, preferably selected from sulfonates and carboxylates. Anionic surfactants also may have polymerized residues of ethylene oxide, and/or may have aromatic rings, e.g., linear alkylbenzene sulfonates. Some anionic surfactants are fatty acid alkali metal salts. In one preferred embodiment of the invention, the detergent composition comprises at least 4 wt % linear alkylbenzene sulfonates, preferably at least 5 wt %; preferably no more than 12 wt %, preferably no more than 10 wt %. In another preferred embodiment of the invention, the detergent composition comprises at least 15 wt % linear alkylbenzene sulfonates, preferably at least 18 wt %; preferably no more than 30 wt %, preferably no more than 28 wt %, preferably no more than 26 wt %. Preferably, alkylbenzene sulfonates have a $C_{10}$-$C_{14}$ alkyl group. In a preferred embodiment of the invention, the detergent composition comprises at least 3 wt % alkyl sulfate ethoxylates, preferably at least 4 wt %, preferably at least 6 wt %, preferably at least 8 wt %; preferably no more than 16 wt %, preferably no more than 14 wt %, preferably no more than 10 wt %, preferably no more than 7 wt %. Preferably, an alkyl sulfate ethoxylate comprises an alkyl group (preferably $C_{12}$-$C_{13}$), polymerized ethylene oxide units and a sulfate group. Preferably, an alkyl sulfate ethoxylate contains from one to five polymerized ethylene oxide units per molecule.

Preferably, when the detergent composition is in liquid form it has a pH from 6 to 12.5; preferably at least 6.5, preferably at least 7, preferably at least 7.5; preferably no greater than 12.25, preferably no greater than 12, preferably no greater than 11.5. Suitable bases to adjust the pH of the formulation include mineral bases such as sodium hydroxide (including soda ash) and potassium hydroxide; sodium bicarbonate, sodium silicate, ammonium hydroxide; and organic bases such as mono-, di- or tri-ethanolamine; or 2-dimethylamino-2-methyl-1-propanol (DMAMP). Mixtures of bases may be used. Suitable acids to adjust the pH of the aqueous medium include mineral acid such as hydrochloric acid, phosphorus acid, and sulfuric acid; and organic acids such as acetic acid. Mixtures of acids may be used. The formulation may be adjusted to a higher pH with base and then back titrated to the ranges described above with acid.

Benefits of the composition of this invention include softening, wrinkle reduction/ease of ironing, static control, anti-graying attributes—no adverse impact on ballast load, reduction of "off" odors emanating from cationic cellulosics (a concern with trimethyl analogues), enhanced fragrance deposition, dye transfer inhibition, color fidelity/fastness, reduced fiber abrasion (looking newer longer), improved fiber lubricity (less skin irritation), fiber "fluffiness", shape retention (fiber elasticity) and reduced garment shrinkage.

EXAMPLES

Synthesis of cationically modified hydroxyethyl cellulose, methyl cellulose and hydroxypropyl methyl cellulose. The polymers were characterized for ash and volatiles content as described in ASTM D-2364.

Preparation 1: QUAB 342-modified CELLOSIZE hydroxyethyl Cellulose

A 1000 ml, four-necked, round-bottomed flask was charged with 65.50 g (60.20 g contained) CELLOSIZE QP-100MH hydroxyethyl cellulose and 328 g of acetone. The flask was fitted with a nitrogen inlet, rubber serum cap, a stirring paddle and electric motor, and a Claisen adaptor connected to a 60 ml pressure-equalizing addition funnel and a Friedrich condenser connected to a mineral oil bubbler. The 60 ml pressure-equalizing addition funnel was charged with 62.60 g of 40% aqueous QUAB 342 (3-chloro-2-hydroxypropyl dimethyldodecylammonium chloride). While stirring the slurry, the head space of the flask was purged with a slow, steady flow of nitrogen for one hour to remove any entrained oxygen in the apparatus. A flow rate of about one bubble per second is sufficient.

While stirring the slurry under nitrogen, 9.64 g of 50% aqueous sodium hydroxide solution were added dropwise using a plastic syringe over 3 minutes. After stirring for 40 minutes, the 40% aqueous solution of QUAB 342 was added dropwise under nitrogen over 15 minutes. The slurry was stirred for 30 minutes under nitrogen, and then heat was applied using a heating mantle. While stirring under nitrogen, the slurry was refluxed for 3 hours.

The slurry was then cooled in a water bath while maintain a positive nitrogen pressure in the flask. The slurry was neutralized by adding 8.50 g of glacial acetic acid using a syringe and allowing the mixture to stir for 10 minutes. The polymer was recovered by vacuum filtration through a large fritted Buchner funnel. The filter cake was washed in the Buchner funnel by stirring the slurry in the funnel for three minutes with the specified wash solvent followed by vacuum removal of the wash liquor: five times with a mixture of 400 ml of acetone and 80 ml of water, and three times with 450 ml of pure acetone. To confer cold-water dispersibility on the final polymer, 1.00 g of 40% aqueous glyoxal and 0.20 g of glacial acetic acid were added to the final acetone desiccation. The polymer was recovered by vacuum filtration, briefly air dried, and dried overnight in vacuo at 50° C.

The polymer was obtained as an off-white solid (73.4 g), with a volatiles content of 2.2%, an ash content (as sodium acetate) of 5.3%, and a Kjeldahl nitrogen content (corrected for ash and volatiles) of 0.675% (degree of substitution of 0.142). The 1.0% solution viscosity (corrected for ash and volatiles) was measured at 6.31 sec-1 using a TA Instruments DHR-3 rheometer equipped with a 60 mm, 0.5° stainless steel cone & plate sensor at 25.0° C. and was found to be 8350 mPa-sec.

QUAB 342-modified CELLOSIZE ER-52M and QUAB 342-modified CELLOSIZE QP-4400H were made following the procedure described above.

Preparation 2: QUAB 151-modified METHOCEL K4M hydroxypropyl methyl Cellulose A 500 ml, four-necked, round-bottomed flask was charged with 31.82 g (30.68 g contained) METHOCEL K4M hydroxypropyl methyl cellulose and a mixture of 158 g of acetone and 26 g of distilled water. The flask was fitted with a nitrogen inlet, rubber serum cap, a stirring paddle and electric motor, and a Friedrich condenser connected to a mineral oil bubbler. While stirring the slurry, the head space of the flask was purged with a slow, steady flow of nitrogen for one hour to remove any entrained oxygen in the apparatus. A flow rate of about one bubble per second is sufficient.

While stirring the slurry under nitrogen, 2.00 g of 25% aqueous sodium hydroxide solution were added dropwise using a plastic syringe over 3 minutes. After stirring for 60 minutes, 8.54 g of 70% aqueous QUAB 151 (glycidyl trimethylammonium chloride) were added dropwise under nitrogen over 2 minutes using a plastic syringe. The slurry was stirred for 30 minutes under nitrogen, and then heat was applied using a heating mantle. While stirring under nitrogen, the slurry was refluxed for 3 hours.

The slurry was then cooled in a water bath while maintain a positive nitrogen pressure in the flask. The slurry was neutralized by adding 4.10 g of glacial acetic acid using a syringe and allowing the mixture to stir for 10 minutes. The polymer was recovered by vacuum filtration through a large fritted Buchner funnel. The filter cake was washed in the Buchner funnel by stirring the slurry in the funnel for three minutes with the specified wash solvent followed by vacuum removal of the wash liquor: three times with a mixture of 300 ml of acetone and 30 ml of water, once with a mixture of 300 ml of acetone and 20 ml of water, and twice with 300 ml of pure acetone. To confer cold-water dispersibility on the final polymer, 0.50 g of 40% aqueous glyoxal and 0.20 g of glacial acetic acid were added to the final acetone desiccation. The polymer was recovered by vacuum filtration, briefly air dried, and dried overnight in vacuo at 50° C.

The polymer was obtained as an off-white solid (33.3 g), with a volatiles content of 3.3%, an ash content (as sodium acetate) of 1.2%, and a Kjeldahl nitrogen content (corrected for ash and volatiles) of 1.34% (degree of substitution of 0.218). The 2.0% solution viscosity (corrected for ash and volatiles) was measured at 6.31 sec-1 using a TA Instruments DHR-3 rheometer equipped with a concentric cylinder sensor at 25.0° C. and was found to be 1650 mPa-sec.

QUAB 151-modified METHOCEL K100M, QUAB 151-modified METHOCEL F4M and QUAB 151-modified METHOCEL K15M were made following the procedure described above.

Preparation 3: QUAB 151-modified METHOCEL A4M methyl Cellulose

A 500 ml, four-necked, round-bottomed flask was charged with 31.01 g (30.06 g contained) METHOCEL A4M methyl cellulose and a mixture of 158 g of acetone and 16 g of distilled water. The flask was fitted with a nitrogen inlet, rubber serum cap, a stirring paddle and electric motor, and a Friedrich condenser connected to a mineral oil bubbler. While stirring the slurry, the head space of the flask was purged with a slow, steady flow of nitrogen for one hour to remove any entrained oxygen in the apparatus. A flow rate of about one bubble per second is sufficient.

While stirring the slurry under nitrogen, 3.85 g of 25% aqueous sodium hydroxide solution were added dropwise using a plastic syringe over 3 minutes. After stirring for 60 minutes, 8.48 g of 70% aqueous QUAB 151 (glycidyl trimethylammonium chloride) were added dropwise under nitrogen over 2 minutes using a plastic syringe. The slurry was stirred for 15 minutes under nitrogen, and then heat was applied using a heating mantle. While stirring under nitrogen, the slurry was refluxed for 2 hours.

The slurry was then cooled in a water bath while maintain a positive nitrogen pressure in the flask. The slurry was neutralized by adding 8.25 g of glacial acetic acid using a syringe and allowing the mixture to stir for 10 minutes. The polymer was recovered by vacuum filtration through a large fritted Buchner funnel. The filter cake was washed in the Buchner funnel by stirring the slurry in the funnel for three minutes with the specified wash solvent followed by vacuum removal of the wash liquor: once with 500 ml of acetone, twice with a mixture of 450 ml of acetone and 25 ml of water, once with 500 ml of acetone, once with a mixture of 450 ml of acetone and 25 ml of water, once with 500 ml of acetone, twice with a mixture of 450 ml of acetone and 25 ml of water, and twice with 500 ml of pure acetone. To confer cold-water dispersibility on the final polymer, 0.50 g of 40% aqueous glyoxal and 0.25 g of glacial acetic acid were added to the final acetone desiccation. The polymer was recovered by vacuum filtration, briefly air dried, and dried overnight in vacuo at 50° C.

The polymer was obtained as an off-white solid (34.1 g), with a volatiles content of 2.4%, an ash content (as sodium acetate) of 3.0%, and a Kjeldahl nitrogen content (corrected for ash and volatiles) of 1.33% (degree of substitution of 0.207). The 2.0% solution viscosity (corrected for ash and volatiles) was measured at 6.31 sec-1 using a TA Instruments DHR-3 rheometer equipped with a 60 mm, 0.5° stainless steel cone & plate sensor at 25.0° C. and was found to be 2230 mPa-sec.

Preparation 4: QUAB 342-modified METHOCEL K100M hydroxypropyl methyl Cellulose

A 500 ml, four-necked, round-bottomed flask was charged with 30.89 g (30.06 g contained) METHOCEL K100M hydroxypropyl methyl cellulose and 158 g of acetone. The flask was fitted with a nitrogen inlet, rubber serum cap, a stirring paddle and electric motor, and a Claisen adaptor connected to a 60 ml pressure-equalizing addition funnel and a Friedrich condenser connected to a mineral oil bubbler. The 60 ml pressure-equalizing addition funnel was charged with 21.62 g of 40% aqueous QUAB 342 (3-chloro-2-hydroxypropyl dimethyldodecylammonium chloride). While stirring the slurry, the head space of the flask was purged with a slow, steady flow of nitrogen for one hour to remove any entrained oxygen in the apparatus. A flow rate of about one bubble per second is sufficient.

While stirring the slurry under nitrogen, 3.00 g of 50% aqueous sodium hydroxide solution were added dropwise using a plastic syringe over 3 minutes. After stirring for 60 minutes, heat was applied to the slurry using a heating mantle, and the mixture was heated to reflux. The 40% aqueous solution of QUAB 342 was added dropwise under nitrogen over 3 minutes. While stirring under nitrogen, the slurry was refluxed for 3 hours.

The slurry was then cooled in a water bath while maintain a positive nitrogen pressure in the flask. The slurry was neutralized by adding 5.00 g of glacial acetic acid using a syringe and allowing the mixture to stir for 10 minutes. The polymer was recovered by vacuum filtration through a large fritted Buchner funnel. The filter cake was washed in the Buchner funnel by stirring the slurry in the funnel for three minutes with the specified wash solvent followed by vacuum removal of the wash liquor: once with a mixture of 500 ml of acetone and 50 ml of water, twice with a mixture of 300 ml of acetone and 30 ml of water, and twice with 300 ml of pure acetone. To confer cold-water dispersibility on the final polymer, 0.65 g of 40% aqueous glyoxal and 0.20 g of glacial acetic acid were added to the final acetone desiccation. The polymer was recovered by vacuum filtration, briefly air dried, and dried overnight in vacuo at 50° C.

The polymer was obtained as an off-white solid (32.5 g), with a volatiles content of 3.2%, an ash content (as sodium acetate) of 2.8%, and a Kjeldahl nitrogen content (corrected for ash and volatiles) of 0.375% (degree of substitution of 0.058). The 1.0% solution viscosity (corrected for ash and volatiles) was measured at 6.31 sec-1 using a TA Instruments DHR-3 rheometer equipped with a concentric cylinder sensor at 25.0° C. and was found to be 6250 mPa-sec.

QUAB 342-modified METHOCEL K4M was made following the procedure described above.

Preparation 5: QUAB 426-modified CELLOSIZE HEC-59

A 500 ml, four-necked, round-bottomed flask was charged with 31.57 g (27.90 g contained) CELLOSIZE HEC-59 hydroxyethyl cellulose and 163 g of acetone. The flask was fitted with a nitrogen inlet, rubber serum cap, a stirring paddle and electric motor, and a Claisen adaptor connected to a 60 ml pressure-equalizing addition funnel and a Friedrich condenser connected to a mineral oil bubbler. The 60 ml pressure-equalizing addition funnel was charged with 42.02 g of 38% aqueous QUAB 426 (3-chloro-2-hydroxypropyl dimethyloctadecylammonium chloride). While stirring the slurry, the head space of the flask was purged with a slow, steady flow of nitrogen for one hour to remove any entrained oxygen in the apparatus. A flow rate of about one bubble per second is sufficient.

While stirring the slurry under nitrogen, 13.02 g of 25% aqueous sodium hydroxide solution were added dropwise using a plastic syringe over 3 minutes. After stirring for 40 minutes, the 38% aqueous solution of QUAB 426 was added dropwise under nitrogen over 15 minutes. The slurry was stirred for 30 minutes under nitrogen, and then heat was applied using a heating mantle. While stirring under nitrogen, the slurry was refluxed for 3 hours.

The slurry was then cooled in a water bath while maintaining a positive nitrogen pressure in the flask. The slurry was neutralized by adding 7.50 g of glacial acetic acid using a syringe and allowing the mixture to stir for 10 minutes. The polymer was recovered by vacuum filtration through a large fritted Buchner funnel. The filter cake was washed in the Buchner funnel by stirring the slurry in the funnel for three minutes with the specified wash solvent followed by vacuum removal of the wash liquor: three times with a mixture of 400 ml of acetone and 80 ml of water, and twice a mixture of 400 ml of acetone and 50 ml of water, and twice with 450 ml of pure acetone. To confer cold-water dispersibility on the final polymer, 0.33 g of 40% aqueous glyoxal and 0.11 g of glacial acetic acid were added to the final acetone desiccation. The polymer was recovered by vacuum filtration, briefly air dried, and dried overnight in vacuo at 50° C.

The polymer product was obtained as an off-white solid (25.92 g), with a volatiles content of 2.2%, an ash content (as sodium acetate) of 4.9%, and a Kjeldahl nitrogen content (corrected for ash and volatiles) of 0.103% (degree of substitution of 0.018). The 2.0% solution viscosity (corrected for ash and volatiles) was measured at 6.31 sec-1 using a TA Instruments DHR-3 rheometer equipped with a concentric cylinder sensor at 25.0° C. and was found to be 2026 mPa-sec.

Preparation 6: QUAB 342-modified hydrophobe-modified hydroxyethyl Cellulose

A 500 ml, four-necked, round-bottomed flask was charged with 33.44 g (30.00 g contained) hydrophobe-modified hydroxyethyl cellulose ("hmHEC"; hexadecyl, DS=0.0051 and 1% viscosity=6900 mPa-sec) and a mixture of 163 g of acetone and 5 g of distilled water. The hydrophobe-modified hydroxyethyl cellulose was prepared as described in Example 10 of WO 2012/021625. The flask was fitted with a nitrogen inlet, rubber serum cap, a stirring paddle and electric motor, and a Claisen adaptor connected to a 60 ml pressure-equalizing addition funnel and a Friedrich condenser connected to a mineral oil bubbler. The 60 ml pressure-equalizing addition funnel was charged with 19.84 g of 40% aqueous QUAB 342 (3-chloro-2-hydroxypropyl dimethyldodecylammonium chloride). While stirring the slurry, the head space of the flask was purged with a slow, steady flow of nitrogen for one hour to remove any entrained oxygen in the apparatus. A flow rate of about one bubble per second is sufficient.

While stirring the slurry under nitrogen, 7.00 g of 25% aqueous sodium hydroxide solution were added dropwise using a plastic syringe over 3 minutes. After stirring for 40 minutes, the 40% aqueous solution of QUAB 342 was added dropwise under nitrogen over 15 minutes. The slurry was stirred for 30 minutes under nitrogen, and then heat was applied using a heating mantle. While stirring under nitrogen, the slurry was refluxed for 3 hours.

The slurry was then cooled in a water bath while maintaining a positive nitrogen pressure in the flask. The slurry was neutralized by adding 4.10 g of glacial acetic acid using a syringe and allowing the mixture to stir for 10 minutes. The polymer was recovered by vacuum filtration through a large fritted Buchner funnel. The filter cake was washed in the Buchner funnel by stirring the slurry in the funnel for three minutes with the specified wash solvent followed by vacuum removal of the wash liquor: three times with a mixture of 400 ml of acetone and 80 ml of water, and twice a mixture of 400 ml of acetone and 50 ml of water, and twice with 450 ml of pure acetone. The polymer was recovered by vacuum filtration, briefly air dried, and dried overnight in vacuo at 50° C.

The polymer was obtained as an off-white solid (29.26 g), with a volatiles content of 0.8%, an ash content (as sodium acetate) of 2.4%, and a Kjeldahl nitrogen content (corrected for ash and volatiles) of 0.416% (degree of substitution of 0.082). The 1.0% solution viscosity (corrected for ash and volatiles) was measured at 6.31 sec$^{-1}$ using a TA Instruments DHR-3 rheometer equipped with a concentric cylinder sensor at 25.0° C. and was found to be 4156 mPa-sec.

Approximate molecular weight (Mw) values (±5%) for cellulose ethers

| | |
|---|---|
| CELLOSIZE HEC-59 | 250,000 |
| CELLOSIZE QP-100MH | 1,600,000 |
| CELLOSIZE QP-4400H | 1,000,000 |
| CELLOSIZE ER-52M | 1,400,000 |
| hmHEC | 1,300,000 |
| METHOCEL K4M | 1,000,000 |
| METHOCEL F4M | 1,000,000 |
| METHOCEL A4M | 1,000,000 |
| METHOCEL K100M | 1,500,000 |

Functionalization of these cellulose ethers within the limits of the present invention increases Mw by about 10 to 15%.

Evaluation of Modified Cellulose Polymers

A broad array of fabrics was laundered in top loader washing machines utilizing a standard 6 lb. ballast load and typical (North American) washing conditions. The ballast load was comprised of large cotton and polyester (PE)/cotton garments (3'×3'), cotton T-shirts, 12"×12" terry cotton towels (to assess softening), a number of 11"×11" fabrics including cotton percale and 65/35 PE/cotton (to assess wrinkle reduction) and a group of synthetic garments (nylon, polyester) to test for anti-static benefits. Terry cotton cloths were removed after 1 and 3 cycles, respectively, then assessed for softening by a select group of panelists in a blind study. Internal controls (harsh and soft garments) were placed alongside four laundered pairs of terry cloth towels, and a ranking system of 1-10 was employed (1=harsh, 10=soft). Panelists individually evaluated towels and recorded their observations, and the data is captured in the tables below.

In an independent assessment, cotton percale and polyester/cotton cloths were evaluated for crease reduction (CR), utilizing the following AATCC 124 test methodology based upon a 1-5 scale. A rating of 1 indicates a highly creased fabric as compared to a rating of 5, which appears to have been ironed and is crease free. The degree of substitution (DS) listed for the modified cellulose ethers indicates the degree of quaternary ammonium substitution.

TABLE A1

Impact of cationic cellulosics on softening through the wash. ULTRA SNUGGLE added during the rinse cycle

| | Softening (1 cycle) Terry Cotton | Softening (3 cycles) Terry Cotton | CR Cotton Percale | CR PE/Cotton |
|---|---|---|---|---|
| Harsh Control | 1.0 | 1.0 | | |
| 90% Active Generic Unit Dose HDL (20 grams std. dosage/load) | 3.1 | 3.4 | 2.0 | 4.0 |
| 90% Active Generic Unit Dose HDL + 3% UCARE LR-400 | 4.3 | 5.2 | 3.0 | 4.0 |
| 90% Active Generic Unit Dose HDL + 3% QUAB 342-modified CELLOSIZE HEC ER-52M, DS = 0.131 | 5.1 | 6.0 | 3.5 | 4.0 |

TABLE A1-continued

Impact of cationic cellulosics on softening through the wash. ULTRA SNUGGLE added during the rinse cycle

| | Softening (1 cycle) Terry Cotton | Softening (3 cycles) Terry Cotton | CR Cotton Percale | CR PE/ Cotton |
|---|---|---|---|---|
| 90% Active Generic Unit Dose HDL + ULTRA SNUGGLE (20 grams/load) | 7.6 | 7.9 | 2.5 | 4.0 |
| Soft Control | 10 | 10 | | |

TABLE A2

Impact of cationic cellulosics on softening through the wash. Ultra SNUGGLE added during the rinse cycle

| | Softening (1 cycle) Terry Cotton | Softening (3 cycles) Terry Cotton | CR Cotton Percale | CR PE/ Cotton |
|---|---|---|---|---|
| Harsh Control | 1.0 | 1.0 | | |
| 22% Active Generic HDL (56 grams std. dosage/load) | 3.3 | 3.5 | 2.0 | 4.0 |
| 22% Active Generic HDL + 1% UCARE LR-400 | 4.1 | 5.1 | 3.0 | 4.0 |
| 22% Active Generic HDL + 1% QUAB 342-modified CELLOSIZE HEC ER-52M, DS = 0.131 | 5.2 | 5.9 | 3.5 | 4.0 |
| 22% Active Generic HDL + Ultra SNUGGLE (20 grams/load) | 7.6 | 8.0 | 2.5 | 4.0 |
| Soft Control | 10 | 10 | | |

TABLE A3

Impact of cationic cellulosics on softening in a rinse added fabric softener (RAFS) composition

| | Softening (1 cycle) Terry Cotton | Softening (3 cycles) Terry Cotton | CR Cotton Percale | CR PE/ Cotton |
|---|---|---|---|---|
| Harsh Control | 1.3 | 1.3 | | |
| PUREX FREE CLEAR (56 g/load) | 4.1 | 4.3 | 2.5 | 4.0 |
| PFC + 3% STEPANTEX VL-90A (60 g std. dosage/load) | 5.2 | 6.1 | 2.3 | 4.0 |
| PFC + 3% VL-90A (std. dosage) + 1% QUAB 342-modified CELLOSIZE HEC QP-4400H, DS = 0.140 | 6.1 | 8.4 | 3.5 | 4.0 |
| PFC + 3% VL-90A (40 g/load) + 1% QUAB 342-modified CELLOSIZE HEC QP-4400H, DS = 0.140 | 6.0 | 6.4 | 3.0 | 4.0 |
| Soft Control | 9.8 | 9.8 | | |

TABLE A4

Impact of cationic cellulosics on softening in a rinse added fabric softener (RAFS) composition

| | Softening (1 cycle) Terry Cotton | Softening (3 cycles) Terry Cotton | CR Cotton Percale | CR PE/ Cotton |
|---|---|---|---|---|
| Harsh Control | 1.3 | 1.3 | | |
| All Oxi-Stainlifter (56 g/load) | 3.6 | 4.0 | 2.0 | 4.0 |
| AOSL + ULTRA SNUGGLE (20 g/load) | 6.3 | 6.9 | 2.5 | 4.0 |
| AOSL + 3% VL-90A (60 g std. dosage/load) | 4.9 | 5.5 | 2.5 | 4.0 |

TABLE A4-continued

Impact of cationic cellulosics on softening in a
rinse added fabric softener (RAFS) composition

| | Softening (1 cycle) Terry Cotton | Softening (3 cycles) Terry Cotton | CR Cotton Percale | CR PE/ Cotton |
|---|---|---|---|---|
| AOSL + 3% VL-90A (std. dosage) + 1% QUAB 342-modified CELLOSIZE HEC QP-4400H, DS = 0.140 | 6.8 | 7.9 | 3.0 | 4.0 |
| Soft Control | 9.9 | 9.9 | | |

PUREX FREE AND CLEAR is a liquid laundry detergent containing approximately 12-14 wt % surfactant. Approximately 5-10 wt % of the liquid laundry detergent is alcohol sulfate ethoxylate having $C_{10}$-$C_{16}$ alkyl groups and two ethylene oxide units; alcohol ethoxylates and alkylbenzene sulfonic acid salts are also present, each at a level from 1-5 wt %.

STEPANTEX VL 90 A is a cationic surfactant (Methyl bis[ethyhl(tallowate)]-2-hydroxyethyl ammonium methyl sulfate) providing excellent softening, good antistatic and rewetting properties. It is used in most commercial RAFS in North America today.

TABLE A5

Effect of Degree of Cationic Substitution
(All Samples CELLOSIZE QP-100MH/QUAB 342)

| | Softening (1 cycle) Terry Cotton | Softening (3 cycles) Terry Cotton | CR Cotton Percale | CR PE/ Cotton |
|---|---|---|---|---|
| No Cellulosic Polymer | 3.9 | 4.1 | 2.0 | 4.0 |
| Harsh Control | 1.2 | 1.2 | | |
| DS 0.064 | 4.4 | 5.3 | 2.0 | 4.0 |
| DS 0.075 | 4.8 | 5.3 | 2.0 | 4.0 |
| DS 0.086 | 4.9 | 5.9 | 3.0 | 4.0 |
| DS 0.113 | 4.5 | 5.4 | 2.5 | 4.0 |
| DS 0.151 | 5.5 | 6.5 | 2.5 | 4.0 |
| DS 0.177 | 5.9 | 5.9 | 3.5 | 4.0 |
| Soft Control (22% HDL detergent base) | 10 | 10 | | |

TABLE A6

Effect of Degree of Cationic Substitution

| | Softening (1 cycle) Terry Cotton | Softening (3 cycles) Terry Cotton | CR Cotton Percale | CR PE/ Cotton |
|---|---|---|---|---|
| No Cellulosic Polymer | 3.9 | 4.1 | 2.0 | 4.0 |
| CELLOSIZE QP-4400H/ QUAB 342, DS 0.049 | 4.6 | 5.4 | 2.0 | 4.0 |
| CELLOSIZE ER-52M/ QUAB 342, DS 0.131 | 4.9 | 6.0 | 3.5 | 4.0 |
| CELLOSIZE ER-52M/ QUAB 342, DS 0.163 | 4.7 | 5.9 | 3.0 | 4.0 |
| Harsh Control | 1.0 | 1.0 | | |
| Soft Control | 10 | 10 | | |

To assess clay soil anti-redeposition, we utilized four types of fabric (terry cotton, cotton interlock, cotton percale and polyester/cotton blend) and laundered with a variety of commercial and prototypical heavy duty liquid detergents. To cover the broad range of laundry formulations marketed in North America and across the globe, we looked at a variety of commercial heavy duty liquids (HDLs) and a group of prototypical systems to insure we were assessing a broad spectrum of products. The systems were typically comprised of anionic (sodium linear alkyl benzene sulfonate (LABS, Nacconal 90G), sodium lauryl ethoxysulfates (AEOS, Steol CS-460) and nonionic (alcohol ethoxylate, Biosoft N25-7) surfactants in varying ratios, which are representative of low, intermediate and high active (unit dose) formulations. For example, a highly concentrated unit dose formulation based upon 60% Biosoft N25-7 (alcohol ethoxylate), 22% (LABS), 13% Propylene glycol, 2.56% Monoethanolamine (MEA) and the balance water was evaluated with several cellulosics to ascertain performance. An alternative intermediate active formulation based upon 22% total surfactant utilized 6% LABS, 12% AEOS and 4% Nonionic as the active components. Propylene glycol and ethanol were used as hydrotropes to produce a single phase, homogeneous liquid. The lower active formulation (14% ai) was based upon 8% LABS, 4% AEOS and 2% nonionic, and is indicative of several cost formulations marketed in North America. The fabrics were washed in a terg-o-tometer under typical washing conditions (ambient wash temperatures, low/moderate water hardness, 12 minute wash and 3 minute rinse) using a standard detergent dosage (0.88 gram/Liter) and an orange (high iron content) clay slurry as the added soil load. The garments were laundered for three consecutive cycles, and the whiteness index was measured at 460 nm utilizing a HunterLab UltraScan VIS Colorimeter to determine fabric whiteness in accordance with ASTM E313. The data is in a series of tables for PUREX FREE CLEAR, ALL STAINLIFTER and Tide with a Touch of DOWNY liquid detergent. The whiteness index for the neat unwashed fabrics is represented in the tables (positive control), and internal controls were also run for the neat detergent (Purex/All/Tide) with and without the added cellulosics. As depicted in patent application WO2014052396A1, the non-derivitized HECs (Cellosize HEC QP-300, QP-4400H and QP-100MH) have minimal adverse impact on fabric whiteness maintenance.

Three sets of different cellulosic backbone molecular weights were synthesized (low, intermediate and high), and the polymers were evaluated for clay soil redeposition. The use of a low molecular weight cellulosic backbone has a dramatic, adverse impact on the whiteness index on cotton garments (interlock, percale and terry). The intermediate/high molecular weight polymers unexpectedly deliver whiteness maintenance comparable to the neat liquid detergent w/o additive.

TABLE I

Impact of cellulosic backbone molecular weight on clay soil anti-redeposition

| | Cotton Interlock WI E313 | Cotton Percale WI E313 | Cotton Terry WI E313 | PE/Cotton WI E313 |
|---|---|---|---|---|
| Stripped Cloth | 115 | 87 | 145 | 115 |
| PFC + 1% QUAB 342 modified HEC-59, DS = 0.044 | 58 | 77 | 106 | 80 |
| PFC + 1% QUAB 426 modified HEC-59, DS = 0.015) | 92 | 81 | 115 | 85 |
| PFC + 1% QUAB 426 modified HEC QP-100MH, DS = 0.026) | 120 | 95 | 139 | 87 |
| PFC + 1% QUAB 342 modified HEC QP-4400H, DS = 0.049 | 114 | 90 | 135 | 78 |
| Purex Free Clear HDL - No Additive | 120 | 91 | 137 | 76 |

In the next two series of assessments, the nature of cationic substitution was varied. Three different cationic moieties were tested (trimethyl, dodecyl dimethyl and octadecyl dimethyl quats), and the polymers were once again evaluated for clay soil redeposition. Commercial cationic cellulosics utilize trimethyl quats (QUAB 151), which have a dramatic, adverse impact on the whitening index on cotton garments (interlock, percale and terry). The more phobic dodecyl (QUAB 342) and octadecyl (QUAB 426) analogues unexpectedly deliver whiteness maintenance values that are comparable to the neat liquid detergent w/o additive while delivering softening, crease reduction and anti-static properties.

TABLE II

Impact of cationic moiety on clay soil anti-redeposition

| | Cotton Interlock WI E313 | Cotton WI E313 | Terry WI E313 | PE/Cotton WI E313 |
|---|---|---|---|---|
| Stripped Cloth | 125 | 81 | 148 | 117 |
| Purex Free Clear HDL - No Additive | 111 | 89 | 131 | 79 |
| PFC + 1% QUAB 342 modified Methocel K4M, DS = 0.072 | 116 | 88 | 136 | 73 |
| PFC + 1% QUAB 426 modified Methocel K4M, DS = 0.061 | 118 | 93 | 132 | 75 |
| PFC + 1% QUAB 151 modified Methocel K4M, DS = 0.196) | 45 | 55 | 63 | 83 |
| PFC + 1% QUAB 151 modified Methocel K100M, DS = 0.059 | 30 | 57 | 44 | 82 |
| PFC + 1% QUAB 342 modified HEC QP-100MH, DS = 0.0694 | 114 | 97 | 135 | 70 |

TABLE III

Impact of cationic moiety on clay soil anti-redeposition

| | Cotton Interlock WI E313 | Cotton WI E313 | Terry WI E313 | PE/Cotton WI E313 |
|---|---|---|---|---|
| Stripped Cloth | 133 | 85 | 146 | 115 |
| PFC + 1% QUAB 151 modified F4M, DS = 0.091 | 29 | 65 | 53 | 74 |
| PFC + 1% QUAB 151 modified F4M, DS = 0.158 | 27 | 46 | 53 | 71 |
| PFC + 1% QUAB 151 modified K15M, DS = 0.202 | 50 | 74 | 71 | 71 |
| Purex Free Clear HDL - No Additive | 114 | 87 | 130 | 72 |
| PFC + 1% QUAB 342 modified hmHEC, DS = 0.082 | 110 | 88 | 130 | 76 |

Table IV depicts the performance of a number of commercial cellulosics utilizing trimethyl quats as the principle cationic moiety. Once again, performance is noticeably poorer than the no-additive control.

TABLE IV

Performance of commercial cationic cellulosics on clay soil anti-redeposition

|  | Cotton Interlock WI E313 | Cotton WI E313 | Terry WI E313 | PE/ Cotton WI E313 |
|---|---|---|---|---|
| Stripped Cloth | 118 | 87 | 149 | 118 |
| Purex Free Clear HDL - No Additive | 110 | 87 | 125 | 65 |
| PFC + 1% SoftCat SL-5 | 69 | 76 | 107 | 48 |
| PFC + 1% SoftCat SX-400H | 52 | 68 | 79 | 78 |

TABLE IV-continued

Performance of commercial cationic cellulosics on clay soil anti-redeposition

|  | Cotton Interlock WI E313 | Cotton WI E313 | Terry WI E313 | PE/ Cotton WI E313 |
|---|---|---|---|---|
| PFC + 1% SoftCat SX-1300H | 61 | 62 | 84 | 67 |
| PFC + 1% UCARE LK | 27 | 50 | 60 | 70 |

Table V illustrates the performance of a number of commercial heavy duty liquid detergents, washed in the presence/absence of a rinse added fabric softener, cationic cellulosic (54-5) or a non-cellulosic cationic polymer (Tide with a Touch of DOWNY). The incorporation of a dodecyl, dimethyl quaternary ammonium substituent on a high molecular weight cellulosic backbone delivers excellent clay soil anti-redeposition properties when utilized in a through the wash application. Improved softening and reduced wrinkling are also clearly observed. The commercial 2-in-1 detergent (TTD) has a noticeably poorer whiteness maintenance profile across the fabric spectrum (various cottons, polyester/cotton garments).

TABLE V

Performance of cationic cellulosics versus a commercial 2-in-1 heavy duty liquid detergent on clay soil anti-redeposition

|  | Cotton Interlock WI E313 | Cotton WI E313 | Terry WI E313 | PE/ Cotton WI E313 |
|---|---|---|---|---|
| Stripped Cloth | 84 | 81 | 146 | 107 |
| ALL STAINLIFTER | 123 | 111 | 142 | 109 |
| ALL STAINLIFTER + SNUGGLE (added during the rinse) | 100 | 106 | 123 | 104 |
| ALL STAINLIFTER + 1% QUAB 342-modified CELLOSIZE HEC ER-52M, DS = 0.131 | 128 | 114 | 144 | 111 |
| ALL STAINLIFTER + 1% QUAB 342-modified CELLOSIZE HEC ER-52M, DS = 0.131 + SNUGGLE | 102 | 103 | 124 | 101 |
| TIDE with a Touch of DOWNY | 64 | 95 | 84 | 83 |
| TIDE with a Touch of DOWNY + APRIL FRESH DOWNY (added during the rinse) | 66 | 98 | 86 | 87 |

Table VI depicts the performance of a number of experimental cellulosics with a high degree of cationic substitution (DS). There is minimal difference in the performance of these materials and the Purex Free Clear internal control.

TABLE VI

Performance of various cellulosics with a high degree of cationic substitution on clay soil anti-redeposition

|  | Cotton Interlock WI E313 | Cotton WI E313 | Terry WI E313 | PE/ Cotton WI E313 |
|---|---|---|---|---|
| Stripped Cloth | 89 | 81 | 148 | 107 |
| PFC + 1% 24-1 (QUAB 342-modified CELLOSIZE HEC QP-100MH) DS: 0.113 | 69 | 91 | 131 | 87 |
| PFC + 1% 24-2 (QUAB 342-modified CELLOSIZE HEC QP-100MH) DS: 0.151 | 68 | 93 | 133 | 88 |
| PFC + 1% 24-3 (QUAB 342-modified CELLOSIZE HEC QP-100MH) DS: 0.177 | 67 | 94 | 132 | 91 |
| PFC + 1% 24-4 (QUAB 342-modified CELLOSIZE HEC ER-52M) DS: 0.163 | 66 | 90 | 132 | 88 |
| Purex Free Clear HDL - No Additive | 74 | 94 | 135 | 96 |

The cellulosic polymers of the present invention have also been found to enhance the softening and wrinkle reduction properties through the rinse cycle when used in combination with a rinse added fabric softener (containing a cationic surfactant). Evaluations were conducted utilizing commercial rinse added fabric softeners (SNUGGLE and DOWNY, respectively) and a prototypical low active formulation (3% active esterquat, Stepantex VL-90A). By introducing 1% cellulosic into the low active system, softening results are comparable to intermediate/premium grade commercial compositions (Ultra SNUGGLE, Ultra DOWNY).

Dye Transfer Inhibition

To validate our findings, we laundered two standardized color transfer cloths (Acid Red 151 on Nylon, Direct Blue 71 on cotton) provided by Testfabrics, Inc utilizing a modified ASTM D5548-13 test methodology. The cloths were pre-read using a HunterLab UltraScan VIS Colorimeter to record differences in color, measuring the reflectance of the dyed and undyed (white) fabrics in the same manor (front and back). The swatches were then washed in a Terg-o-tometer for one and three cycles, respectively at 35° C., 190 ppm water hardness (2.5:1 Ca/Mg) for 12 minutes, then rinsed in clean water for 3 minutes, air dried (w/o heat) and assessed for color change. We used a prototypical 22% active heavy duty liquid detergent (described below) at 0.69 gram/Liter, with two 3"×4.5" dyed swatches and one undyed cotton swatch/terg pot.

The Prototypical Heavy Duty Laundry (HDL) formulation selected for studying the Dye Transfer inhibition technologies was the following:

| Ingredients | % Active |
|---|---|
| Deionized Water | 50.0 |
| Nacconal 90 (Linear Alkyl Benzene Sulfonate) | 6.0 |
| Steol CS-460 (Sodium Lauryl Ethoxysulfate) | 12.0 |
| Biosoft N25-7 (Nonionic Alcohol Ethoxylate) | 4.0 |
| Propylene Glycol | 3.5 |
| Ethanol | 1.5 |
| Cationic Cellulosic (DTI) | 0.5 |
| NaOH (10%) | Adjust pH to 8.0 |
| Deionized Water | QS to 100 |

The Delta E of each swatch was calculated from the L*a*b* values of unwashed and washed swatch, following the following equation:

$$\Delta E = \sqrt{\{(L^*_{unwashed} - L^*_{washed})^2 + (a^*_{unwashed} - a^*_{washed})^2 + (b^*_{unwashed} - b^*_{washed})^2\}}$$

The higher the value of Delta E, the greater the amount of dye transferred to the white cotton fabric. Lower values indicate that the additive is assisting in controlling fugitive dyes from redepositing back on the "clean" cotton swatch. The data summarized in the table below gives a clear indication of the benefit. There was a very small (positive) difference noted with LTL-5870 on the Direct Blue 71 cloths and a more significant advantage observed on the Acid Red 151 dye after one and three wash cycles, respectively. These notable benefits were observed with both dyes with the mixed (alkyl) quat and trimethyl quaternized analogues (AW-7120 and UCARE JR-30M).

Delta E of bleached cotton print cloth (undyed) after 1 and 3 cycles

| | Red, 1 cycle | Red, 3 cycles | Blue, 1 cycle | Blue, 3 cycles |
|---|---|---|---|---|
| 22% A.I. Base | 12.73 | 13.96 | 16.49 | 19.23 |
| LTL-5870 | 8.30 | 11.79 | 15.83 | 18.99 |
| UCARE LR-30M | 8.24 | 12.23 | 12.07 | 14.36 |
| AW-7120 | 8.69 | 12.26 | 11.57 | 14.58 |

LTL-5870 = CELLOSIZE QP-100MH, QUAB 342 (DS 0.097)
AW-7120 = CELLOSIZE QP-100MH, QUAB 151/342 (DS 0.120/0.034)
UCARE LR-30M = CELLOSIZE QP-100MH, QUAB 151 (DS 0.16-0.22)

Cationic Derivative
QUAB 151=trimethyl quat (R=methyl)
QUAB 342=dodecyl, dimethyl quat

The invention claimed is:

1. A laundry detergent composition comprising at least 40 wt % water; and a modified carbohydrate polymer having quaternary ammonium groups having at least one $C_8$-$C_{22}$ alkyl; wherein the modified carbohydrate polymer has a weight-average molecular weight of at least 500,000; and wherein at least 20 wt % of quaternary ammonium groups on said at least one modified carbohydrate polymer have at least one $C_8$-$C_{22}$ alkyl; wherein the modified carbohydrate polymer is of formula (I)

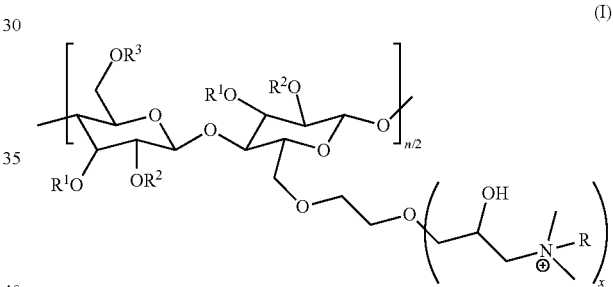

(I)

wherein $R^1$, $R^2$ and $R^3$ are independently selected from hydrogen, alkyl or hydroxyalkyl; wherein alkyl groups may comprise from one to six carbon atoms which may be unsubstituted or substituted with carboxylic acid or salts thereof, halo or $C_{1-4}$ alkoxy;
wherein n is from 25 to 7,500;
wherein R is a $C_{8-22}$ alkyl group; and
wherein x is the degree of substitution of the quarternary ammonium groups.

2. The laundry detergent composition of claim 1 in which said modified carbohydrate polymer is a modified cellulose ether.

3. The laundry detergent of claim 2 having from 0.1 to 3 wt % of said modified cellulose ether.

4. The laundry detergent of claim 3 in which said modified cellulose ether has quaternary ammonium groups which have one $C_{10}$-$C_{22}$ alkyl group.

5. The laundry detergent of claim 4 in which said modified cellulose ether has a weight-average molecular weight from 700,000 to 2,000,000.

6. The laundry detergent of claim 5 in which said modified cellulose ether is a modified hydroxyethyl cellulose.

7. The laundry detergent of claim 6 having total surfactant content from 5 to 60 wt %.

8. The laundry detergent of claim 7 wherein x is from 0.02 to 0.5.

9. The laundry detergent of claim 8 in which at least 50 wt % of quaternary ammonium groups on said at least one modified hydroxyethyl cellulose have one $C_{10}$-$C_{22}$ alkyl group.

10. The laundry detergent of claim 1, wherein the laundry detergent exhibits softening and anti-graying attributes.

* * * * *